United States Patent [19]

Bargiotti et al.

[11] Patent Number: 5,045,534

[45] Date of Patent: Sep. 3, 1991

[54] 4-DEMETHOXY-4'-AMINO-4'-DEOXY-ANTHRACYCLINE DERIVATIVES

[75] Inventors: Alberto Bargiotti; Maria Grandi; Antonino Suarato; Fernando Giuliani, all of Milan, Italy

[73] Assignee: Farmitalia Carlo Erba S.R.L., Milan, Italy

[21] Appl. No.: 501,800

[22] Filed: Mar. 30, 1990

Related U.S. Application Data

[63] Continuation of Ser. No. 266,569, Nov. 3, 1988, abandoned.

[30] Foreign Application Priority Data

Nov. 10, 1987 [GB] United Kingdom ............... 8726272

[51] Int. Cl.$^5$ ................. A01K 31/70; A01N 43/08; C07H 15/24
[52] U.S. Cl. ............................. 514/34; 536/6.4; 536/6.2; 536/17.2
[58] Field of Search .................... 536/6.4, 122; 514/34

[56] References Cited

U.S. PATENT DOCUMENTS

| | | | |
|---|---|---|---|
| 4,046,878 | 9/1977 | Patelli et al. | 514/34 |
| 4,067,969 | 1/1978 | Fenco et al. | 514/34 |
| 4,125,607 | 11/1978 | Arcamone et al. | 514/34 |
| 4,366,149 | 12/1982 | Bargiotti et al. | 514/34 |
| 4,448,724 | 5/1984 | Cava et al. | 552/201 |
| 4,522,815 | 6/1985 | Bargotti et al. | 514/34 |

OTHER PUBLICATIONS

Arcamone et al., Cancer Treatment Reports, vol. 60, No. 7, Jul. 1976, pp. 829–834.
Sammes (Editor), Topics in Antibiotic Chemistry, vol. 2, 1978, pp. 226 and 227.
Chemical Abstracts 1978, vol. 89, No. 13, Abstract No. 99696d, DeMarco et al., Cancer Treat. Rep., vol. 62, No. 3, pp. 375–380.

Primary Examiner—Johnnie R. Brown
Assistant Examiner—Gary L. Kunz
Attorney, Agent, or Firm—Oblon, Spivak, McClelland, Maier & Neustadt

[57] ABSTRACT

Antitumour anthracycline glycosides of formula I:

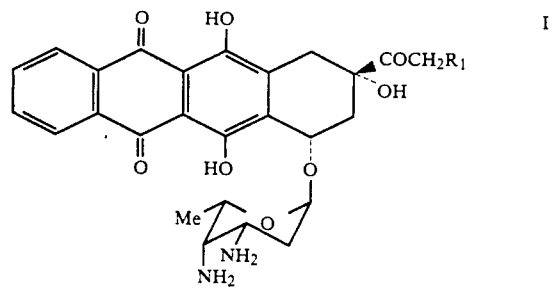

wherein $R_1$ is hydrogen or a hydroxyl group, and pharmaceutically acceptable acid addition salts thereof.

4 Claims, No Drawings

4-DEMETHOXY-4'-AMINO-4'-DEOXY-ANTHRACYCLINE DERIVATIVES

This is a continuation of application Ser. No. 07/266,569, filed on Nov. 3, 1988, now abandoned.

The invention relates to new anthracycline derivatives, to processes for their preparation, and to pharmaceutical compositions containing them.

The invention provides anthracycline glycosides of the general formula I:

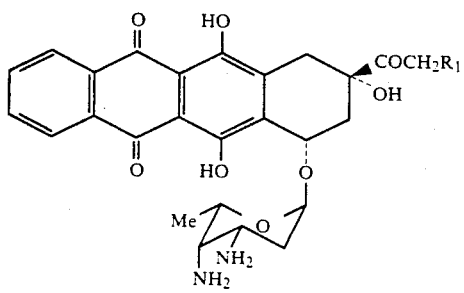

in which $R_1$ represents a hydrogen atom or a hydroxy group, and pharmaceutically acceptable acid addition salts thereof. A preferred salt is the hydrochloride salt.

The compounds of the invention are derivatives of 4-demethoxy-daunorubicin (idarubicin) which is a known antitumor antibiotic. The preferred anthracycline glycosides of formula I are 4-demethoxy-4'-amino-4'-deoxydaunorubicin (I-A) ($I:R_1=H$) and 4-demethoxy-4'-amino-4'-deoxy-doxorubicin (I-B) ($I:R_1=OH$).

The invention also provides a process for the preparation of anthracycline glycosides of formula I or pharmaceutically acceptable acid addition salts thereof, which process comprises:

(i) reacting 4-demethoxy-daunomycinone, a known aglycone of the antitumor anthracycline idarubicin, with 2,3,4,6-tetradeoxy-3,4-ditrifluoroacetamido-L-lyxohexopyranosyl chloride of formula II

(ii) removing the N-trifluoracetyls group from the compound of formula III thus obtained:

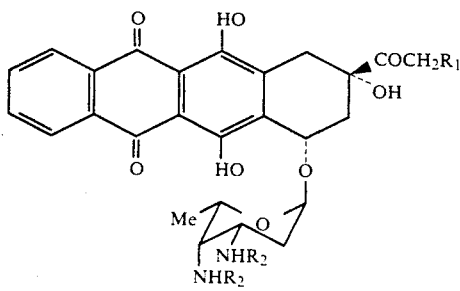

wherein $R_1$ is hydrogen and $R_2$ is $CF_3CO-$, so as to obtain a glycoside of formula I wherein $R_1$ represents hydrogen;

(iii) if desired, converting the said glycoside of formula I into a pharmaceutically acceptable acid addition salt thereof;

(iv) if desired, brominating the said glycoside of formula I or pharmaceutically acceptable acid addition salt thereof and hydrolysing the 14-bromo derivative thus obtained so as to form the corresponding anthracycline glycoside of formula I wherein $R_1$ represents a hydroxy group; and (v) if desired, converting the said glycoside of formula I wherein $R_1$ represents a hydroxy group into a pharmaceutically acceptable acid addition salt thereof.

2,3,4,6-Tetradeoxy-3,4-ditrifluoroacetamido-L-lyxo-hexopyranosyl chloride of formula II can be obtained by the procedure described in U.S. Pat. No. 4,366,149. Step (i) of the present process may be effected by reacting the 4-demethoxy-daunomycinone, dissolved in dry methylene dichloride, at room temperature with the 2,3,4,6-tetradeoxy-3,4-ditrifluoroacetamido-L-lyxo-hexopyranosyl chloride, in the presence of a molecular sieve and silver trifluoromethane sulphonate.

After step (i) but before step (ii) the compound of formula II may be subjected to chromatographic purification on a silica gel column, using as eluent a mixture of methylene dichloride-acetone (97:3 v/v). Step (ii) can be effected by subjecting the compound of formula III to alkaline hydrolysis with 0.2N aqueous sodium hydroxide, at room temperature, under a nitrogen atmosphere and for 1.5 hours.

Step (iii) may be carried out by treating the 4-demethoxy-4'-amino-4'-deoxy-daunorubicin with methanolic hydrogen chloride and isolating the 4-demethoxy-4'-amino-4'-deoxy-daunorubicin as its hydrochloride. Step (iv) can be effected by bromination and mild hydrolysis as described in U.S. Pat. No. 4,112,076. The 14-bromo-derivative can be hydrolysed by treatment with aqueous sodium formate at room temperature. The resultant 4-demethoxy-4'-amino-4'-deoxydoxorubicin is typically isolated as its hydrochloride in step (v) by treatment with methnolic hydrogen chloride.

The present invention also provides pharmaceutical compositions comprising an anthracycline glycoside of formula I or a pharmaceutically acceptable acid addition salt thereof, together with a pharmaceutically acceptable carrier or diluent. Conventional carriers and diluents may be used. The composition may be formulated and administered in conventional manner.

The compounds of formula I and their salts are useful in methods of treatment of the human or animal body by therapy. They are useful as antitumor agents by administering to a human patient a therapeutically effective amount to a patient. An amount sufficient to inhibit the growth of a tumor may be administered. The tumor may be a Colon adenocarcinoma or Gross Leukaemia tumor.

EXAMPLE 1

Preparation of 4-demethoxy-4'-amino-4'-deoxy-daunorubicin (I-A)

Coupling of 4-demethoxy daunomycinone (0.55 g 1.5 mmol) in dry methylene dichloride (75 ml) with 2,3,4,6-tetradeoxy-3,4-ditrifluoroacetamido-L-lyxo-hexopyranosyl chloride (II, 0.43 g, 1.2 mmol) in the presence of molecular sieve (4.A—Merck, 4 g) was performed using silver trifluoromethane sulphonate (0.31 g in 10 ml of dry diethyl ether) as catalyst. After 15 minutes under vigorous stirring at room temperature, the reaction mixture was treated with a saturated aqueous solution of sodium hydrogen carbonate, and the organic phase was then separated off and evaporated under vacuum. Chromatographic purification of the crude residue on a column of silica gel using a 97:3 by volume methylene dichloride:acetone mixture as eluent, gave 4-demethoxy-4'-trifluoroacetamido-4'-deoxy-N-trifluoroacetyldaunorubicin (III, 0.56 g, 68%): m.p. 163°–164° C. (with decomposition).

The PMR spectrum (200 MHz, CDCl$_3$) showed absorptions at 1.24 (d, J=6.6 Hz, 3H, CH$_3$-s'), 2.42 (s, 3H, COCH$_3$), 4.33 (m, 2H, h-3', h-4'), 4.49 (dq, J<1, 4.0 Hz, 1H, H-1'), 5.26 (dd, J=1.8, 4 Hz, 1H, H-7), 5.55 (d, J<1, 4.0 Hz, 1H,H-1'), 5.64 (d, J=7.0 Hz, 1H, NH-COCF$_3$-4'), 6.78 (d, J=6.0 Hz, 1H, NH-COCF$_3$-3') 7.81–7.86 (m, 2H, H-2, H-3), 8.29–8.36 (m, 2H, H-1, H-4), 13.30 (s, 1H, OH-11), 13.63 δ (s, 1H, OH-6). 0.5 g (0.73 mmol) of III in 45 ml of 0.2N aqueous sodium hydroxyde was stirred under nitrogen at room temperature. After 1.5 hours the reaction mixture was acidified (pH 2.5) with aqueous hydrochloric acid and then extracted with methylene dichloride to eliminate some impurities. The aqueous phase was adjusted to pH 8.1, was extracted with methylene dichloride and the extract was washed with water, dried over anhydrous sodium sulphate and concentrated to a small volume. Acidification (pH 4.5) with methanolic hydrogen chloride, followed by addition of diethyl ether, gave 4-demethoxy-4'-amino-4'-deoxy-daunorubicin (I-A, 0.37 g, 90%) as its hydrochloride: m.p. 155°–156° C. (with decomposition).

EXAMPLE 2

Preparation of 4-demethoxy-4'-amino-4'-deoxy-doxorubicin (I-B)

0.2 g of I-A dissolved in a mixture of 2.7 ml of anhydrous methanol and 7.5 ml of dioxane was mixed with 0.2 ml of ethyl orthoformate and 0.75 ml of a solution of 0.94 g of bromine in 10 ml of methylene dichloride.

After 1.5 hours at room temperature, the reaction mixture was poured into a mixture of 40 ml of diethyl ether and 20 ml of petroleum ether. A red precipitate formed, which was filtered and washed several times with diethyl ether to completely remove the acidity. The precipitate was dissolved in a mixture of 6 ml of acetone and 6 ml 0.25N aqueous hydrogen bromide.

After 10 hours at room temperature was added 0.3 g of sodium formate dissolved in 1 ml of water. The reaction mixture was stirred at room temperature for 30 hours, 6 ml of water were added to the mixture and the solution was extracted with methylene dichloride to remove the aglycones. The aqueous phase was added with 5 ml of an 8% aqueous solution of sodium hydrogen carbonate and repeatedly extracted with methylene dichloride. The organic extracts were dried with sodium sulfate and evaporated to a small volume under vacuum.

The resulting red solution adjusted to pH 3.5 with anhydrous methanolic hydrogen chloride, was added with excess ethyl ether to give 0.17 g of 4-demethoxy-4'-amino-4'-deoxy-doxorubicin (I-B), as hydrochloride. m.p. 156°–157° C. (with decomposition).

BIOLOGICAL ACTIVITY

"IN VITRO"

The compounds I-A and I-B were tested "in vitro" as inhibitor of colony growth on two human cell lines: LOVO (colon adenocarcinoma) and LOVO/DX (colon adenocarcinoma resistant to doxorubicin). Both compounds resulted more cytotoxic than the parent drugs, respectively 4'-amino-4'-deoxy daunorubicin and 4'-amino-4'-deoxy doxorubicin, (U.S. Pat. No. 4,366,149) on LOVO and LOVO/DX Table 1). When compared with daunorubicin and doxorubicin a striking higher activity on the doxorubicin-resistant cell line was observed for I-A, 4'-amino-4'-deoxy-daunorubicin, I-B and 4'-amino-4'-deoxy-doxorubicin.

TABLE 1

CYTOTOXIC ACTIVITY ON LOVO AND LOVO/DX - TREATMENT: 4 HRs

| COMPOUND | ID$_{50}$[c] (mg/ml) LOVO | LOVO/DX | R.I.[d] |
|---|---|---|---|
| DOXORUBICIN[a] | 56.5 | 2087 | 36.9 |
| 4'-AMINO-4'-DEOXY-DX[b] | 34.6 | 121.6 | 3.5 |
| I-B[b] | 8.6 | 31.5 | 3.6 |
| DAUNORUBICIN[a] | 42.4 | 2357 | 55.5 |
| 4'-AMINO-4'-DEOXY-DN[b] | 82.5 | 440 | 5.3 |
| I-A[b] | 12.5 | 65.6 | 5.24 |

[a]Data of ten experiments
[b]Data of three experiments
[c]ID$_{50}$ Inhibiting Dose 50%: derived from dose-response curves
[d]R.I. Resistance Index: ratio between ID$_{50}$ on LOVO vs ID$_{50}$ on LOVO/DX

"IN VIVO"

The compounds I-A and I-B were preliminarily tested "in vivo" against Gross disseminated leukemia in mice (Table 2). Both compounds resulted more potent than the parent drugs.

TABLE 2

ACTIVITY AGAINST DISSEMINATED GROSS LEUKEMIA - TREATMENT I.V. ON DAY 1 AFTER TUMOR INOCULATION

| COMPOUND | O.D.[a] (mg/Kg) | T/C %[b] |
|---|---|---|
| DOXORUBICIN | 13 | 200 |
| 4'-AMINO-4'-DEOXY-DX | 26 | 183 |
| I-B | 3.9 | 250 |
| DAUNORUBICIN | 15 | 200 |
| 4'-AMINO-4'-DEOXY-DN | 28 | 185 |
| I-A | 4.4 | 240 |

[a]Optimal dose
[b]Median survival time of treated mice/median survival time of control × 100.

We claim:
1. An anthracycline glycoside of formula I

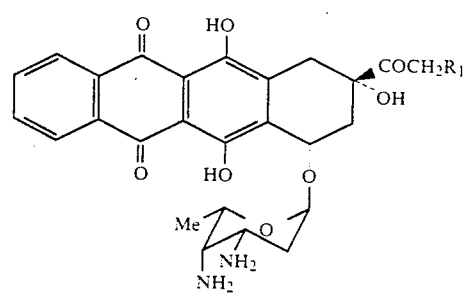

wherein R$_1$ represents a hydrogen atom or a hydroxy group, and pharmaceutically acceptable acid addition salts thereof.

2. The compound according to claim 1, which is 4-demethoxy-4'-amino-4'-deoxy-daunorubicin or its hydrochloride.

3. The compound according to claim 1, which is 4-demethoxy-4'-amino-4'-deoxy-doxorubicin or its hydrochloride.

4. A pharmaceutical composition comprising, as the active ingredient, the anthracycline glycoside of formula I in claim 1 or a pharmaceutically acceptable acid addition salt thereof in combination with a pharmaceutically acceptable diluent or carrier.

* * * * *